US006632471B2

(12) United States Patent
Krause et al.

(10) Patent No.: US 6,632,471 B2
(45) Date of Patent: Oct. 14, 2003

(54) SHEATHS OF MATERIAL HAVING IMPROVED SURFACE BARRIERS

(76) Inventors: Arthur A. Krause, 20539 Archwood St., Winnetka, CA (US) 91306; George H. Carroll, 18080 Boris Dr., Encino, CA (US) 91436

( * ) Notice: Subject to any disclaimer, the term of this patent is extended or adjusted under 35 U.S.C. 154(b) by 53 days.

(21) Appl. No.: 09/770,251

(22) Filed: Jan. 29, 2001

(65) Prior Publication Data

US 2001/0005533 A1 Jun. 28, 2001

Related U.S. Application Data

(63) Continuation-in-part of application No. 09/339,497, filed on Jun. 24, 1999, now abandoned.

(51) Int. Cl.7 .............................................. C23C 16/00
(52) U.S. Cl. ................. 427/2.3; 427/248.1; 427/255.39
(58) Field of Search ............................. 427/248.1, 2.3, 427/255.39

(56) References Cited

U.S. PATENT DOCUMENTS

| | | | |
|---|---|---|---|
| 3,626,517 A | * 12/1971 | Kurtz ............................. 2/167 |
| 3,992,221 A | * 11/1976 | Homsy et al. ................. 134/16 |
| 4,499,154 A | 2/1985 | James et al. | |
| 4,632,842 A | 12/1986 | Karwoski et al. .............. 427/2 |
| 4,935,260 A | 6/1990 | Shlenker .......................... 427/2 |
| 5,079,093 A | 1/1992 | Akashi et al. | |
| 5,149,744 A | 9/1992 | Tarancon ..................... 525/356 |
| 5,242,661 A | 9/1993 | Tarancon ..................... 422/131 |
| 5,357,636 A | 10/1994 | Dresdner, Jr. et al. ....... 2/161.7 |
| 5,474,637 A | 12/1995 | Soodak ..................... 156/272.6 |
| 5,589,563 A | 12/1996 | Ward et al. | |
| 5,671,754 A | 9/1997 | Schmukler et al. | |
| 5,780,112 A | 7/1998 | Pugh et al. .............. 427/393.3 |
| 5,846,604 A | 12/1998 | Caldwell | |
| 5,969,053 A | 10/1999 | Bauman et al. .......... 525/331.5 |

OTHER PUBLICATIONS

Hooper Joseph; "The Soul of the Super Condom", Men's Journal, Apr. 1998 pp. 109–110.

* cited by examiner

*Primary Examiner*—Timothy Meeks
(74) *Attorney, Agent, or Firm*—Dennis H. Lambert

(57) ABSTRACT

A process of treating natural rubber latex articles, such as gloves and condoms, to alter the characteristics of the article so as to improve its barrier properties and resistance to passage of harmful agents therethrough, and the article produced by the process. The article is manufactured in accordance with conventional methods and then treated with a reactive gas, in particular a halogen gas such as fluorine gas, or a mixture of gasses. The treatment is conducted in a sealed chamber in accordance with the protocol of the "Level 1" fluorination treatment performed by Fluoro-Seal, Inc., of Ontario, Calif.

4 Claims, No Drawings

SHEATHS OF MATERIAL HAVING IMPROVED SURFACE BARRIERS

This application is a continuation-in-part of application Ser. No. 09/339,497, filed Jun. 24, 1999 now abandoned.

BACKGROUND OF THE INVENTION

1. Field of the Invention

This invention relates generally to sheaths for the human body. More specifically, the invention relates to protective sheaths which have been treated to enhance the surface barrier properties.

2. Prior Art

The human body and parts thereof are sometimes exposed to harmful agents such as chemicals, viruses, bacteria and other materials capable of causing injury or illness. To reduce the opportunity for injury or illness, a protective sheath or garment may be placed over parts of the body which are exposed to such harmful agents. For example, a mask and/or gloves may be worn by a person who is going to be exposed to dangerous chemicals, viruses, bacteria and other potentially harmful materials.

A glove is an example of a sheath which is ergonomically shaped to cooperate with the human hand, and offers protection by forming a barrier between the hand and harmful agents. Similarly, a condom is a sheath which is ergonomically shaped to cooperate with the penis, and forms a protective barrier against transfer both ways through the condom of fluids and pathogens. It thus prevents transfer of semen and viral matter, e.g., the human immunodeficiency virus (HIV), from the penis into a vagina, and also prevents transfer of fluids and viral matter from the vagina to the penis.

Unfortunately, the effectiveness of a conventional glove or condom in blocking transmission of HIV is not perfect. Because the human immunodeficiency virus is very small, it can pass through high quality latex rubber gloves or condoms, not only through microscopic holes which may exist in the glove or condom, but also by natural penetration or migration through the latex material matrix, which is necessarily porous.

Thus, in order to improve the barrier properties of materials such as latex and silicone rubber, these materials are sometimes treated or modified. This is accomplished in the prior art by forming a lining or coating on the surface of the material. In this way, the beneficial properties associated with latex, e.g., ease of use, low cost and tactile feel, are combined with the improved barrier protection offered by linings or coatings.

For instance, it is possible to place a thin layer of oil or inert powder on a glove to improve its efficacy, or acetate can be used to form a layer on gloves. Each of these added materials offers some improvement in the function of the gloves, but are relatively expensive and introduce foreign material to the glove.

One prior art method of treating gloves is disclosed in U.S. Pat. No. 3,992,221 to HOMSY et al. In this patent, a fluorinating gas is introduced into the glove during manufacture to improve its lubricity. As set forth in column 5, lines 49–52, the treatment must be carried out while the glove is extended by at least 10%, or the desired changes do not occur. There is no mention in this patent of improving the barrier properties of the glove. Instead, the object of the patent is to manufacture a glove having improved lubricity without the use of lubricating or donning powder that is typically used in gloves.

U.S. Pat. No. 5,780,112 to PUGH et al. discloses another method of making a powder-free latex glove, wherein the glove is contacted with a reaction mixture comprising effective amounts of water, an aqueous emulsion comprising a high-density, substantially linear hydrocarbon polymer, and an acid-activated oxidizing agent or initiator, and an effective amount of acid to activate the oxidizing agent or initiator. The reaction is stopped after the appropriate time by introducing a stopping agent, and then neutralized by contacting the article with a neutralizing mixture comprising water and a base. This is a relatively complex and expensive process, and there is no mention of improving the barrier properties of the glove.

In U.S. Pat. No. 4,935,260 to SCHLENKER, a thin chemical barrier is applied to a suit, glove, condom or other sheath to act as a barrier against harmful agents.

Although adding layers of material can be useful in forming or improving the barrier properties of protective sheaths, other methods of treatment or modification of the surface characteristics of rubber or plastic articles are also known. For instance, plastic bottles are sometimes briefly subjected to a flame to alter the surface to improve its characteristics for printing processes.

U.S. Pat. No. 5,671,754 to SCHMUKLER discloses a process in which a condom is charged with electrostatic forces that tend to repel viral material. Although this approach may show some positive effects on improving barrier protection, the cost and complexity may be excessive for use on relatively inexpensive items such as condoms or gloves. In addition, the use of charged particles in connection with condoms presents prospective difficulties relating to electroshock of sensitive parts of the body.

Other known processes for treating materials to improve their performance involves the exposure of the material to a volatile agent which operates to change the surface property and porosity of the material. For instance, plastic bottles are sometimes used to contain solvents whose volatile components are aggressive and may penetrate the wall of the bottle. The alcohol in hairspray, for example, tends to leach through or "boil off" through the plastic. The performance of these bottles may be improved by reducing the surface porosity. This can be accomplished by exposing the surface of the plastic to fluorine gas, which reacts with the plastic to smooth the surface and block access to large pores in the material. Bottles treated in this way are more effective at containing strong solvents and also at preventing migration of materials into the bottle through the wall.

In spite of the existence in the prior art of various processes for treating materials, including gloves and condoms, to improve their barrier properties or to improve lubricity, there remains a need for an inexpensive system and method for treating protective sheaths such as gloves and condoms to improve their barrier properties and resistance to transmission of harmful chemicals and pathogens without the need for applying a separate material layer.

SUMMARY OF THE INVENTION

The present invention is an inexpensive process for treating protective sheaths such as gloves and condoms to improve their barrier properties and resistance to transmission of harmful chemicals and pathogens without the need for applying a separate material layer to the sheath.

The invention includes conventionally manufactured sheaths made of conventional materials, for use in protection of human tissue from exposure or contact with harmful agents, wherein the sheaths are treated with a low level of reactive gas to improve their surface barrier properties.

Articles such as gloves and condoms made of latex rubber are particularly improved by subjecting the article to an environment of a reactive gas such as fluorine, which operates on the latex or other materials to modify the surface of the material to form a greatly improved barrier without the potential problems associated with prior art devices and methods which add layers of foreign material to a base material, or which involve expensive washing procedures and expose the article to a reactive agent in liquid form.

In accordance with the invention, a condom or glove may be manufactured in a conventional process and then subjected to the treatment of the invention. Although the invention is particularly described herein as applied to articles made of latex, e.g., gloves and condoms, many alternative materials are suitable for manufacture of gloves and condoms, and the invention is not necessarily limited to the treatment of articles made from latex.

In the treatment process of the invention, an article is exposed to an environment of reactive gas, i.e., a halogen gas, in suitable concentration, for a suitable period of time, to achieve the desired results. The reactive gas interacts with the material from which the article is made to modify the surface structure of the material.

A condom manufactured conventionally can be treated with the process of the invention by exposing it to a reactive gas to alter the surface characteristics and improve its barrier properties so that undesirable matter such as viruses cannot pass through it.

Similarly, a glove can be manufactured conventionally and then treated with a reactive gas in accordance with the process of the invention to alter its surface characteristics and provide an improved barrier to transmission of matter through it.

In particular, applicants have discovered that latex gloves and condoms can be manufactured conventionally and then placed in a chamber and subjected to a low level fluorination treatment to improve the barrier properties of the gloves or condoms to transmission therethrough of harmful agents. Surprisingly, the treatment can be performed on conventionally manufactured gloves or condoms that are placed in quantity in a box or other container and then located in a fluorinating chamber and subjected to a low level fluorination treatment. It is not necessary to agitate or otherwise specially manipulate the articles in order to achieve the desired results, although the articles can be tumbled or agitated if desired. Thus, a box of gloves or condoms can be simply placed in the chamber and a reactive gas, e.g., fluorine gas, introduced at a predetermined concentration is introduced for a predetermined period of time and at a predetermined pressure and temperature, after which the non-reacted fluorine is evacuated and the gloves or condoms are removed. No further processing of the gloves or condoms is required.

A particular treatment employed in practicing the invention is performed by Fluoro-Seal, Inc., of Ontario, Calif., in their fluorination chamber used for fluorinating bottles and other containers and objects, at their "level 1" treatment. Fluoro-Seal, Inc. uses five treatment levels, ranging from "level 1" to "level 5", with "level 1" being the least intensive and "level 5" being the most intensive. By "intensive" is meant the concentration of fluorine, and/or the temperature, time, and pressure under which the treatment may be carried out. For example, a "level 4" or "level 5" treatment may be used to alter the characteristics of a plastic container for holding acetone.

The particular parameters used in the "level 1" treatment are unknown to applicant at this time because Fluoro-Seal, Inc. chooses to maintain this information confidential. However, the treatment of the invention can be replicated simply by subjecting articles to be treated to Fluoro-Seal's "level 1" treatment. The gloves or condoms are placed in bulk in a box or other container and placed in the fluorination chamber and subjected to the "level 1" treatment. Condoms can be successfully treated even when rolled up.

Definitions

As used herein, the following terms shall have the meanings indicated.

Sheath: As used herein, the term "sheath" is a pliable and durable object made of various materials and into which something may be placed, e.g., a covering which serves as a protective layer, in particular a glove or condom.

Surface Barrier: A surface barrier is a configuration or structure which causes resistance or an increase in resistance to transmission of things across the barrier, or prevents or tends to prevent the passing of things from a first side to a second side of the barrier.

Reactive Gas: Any element, compound or substance in gaseous state or partial gaseous state which is reactive with respect to any other element, compound or substance, in particular a halogen gas.

Fluorine: Fluorine, compositions of fluorine, compounds comprising fluorine, acids of fluorine, fluorides, etc., and compounds and substances that contain any of the preceding are considered "fluorine" for the purposes of this disclosure. It shall be appreciated that a great many variations too numerous to catalogue here may be considered fluorine or compounds or substances which contain fluorine.

Agitation Means: Agitation means is any arrangement provided to move articles about while exposed to a reactive gas in a reaction chamber, whereby their interior surfaces are more readily exposed to reactive gases in the chamber.

DETAILED DESCRIPTION OF THE PREFERRED EMBODIMENTS

In accordance with preferred embodiments of the invention, latex gloves and/or condoms are exposed to low levels of a reactive gas, in particular a halogen, or a combination of gasses, to alter the characteristics of the gloves and/or condoms in a way to improve the barrier to transmission therethrough of chemicals, pathogens and other harmful matter. Exposure of the article to the low levels of a halogen gas, e.g., fluorine gas, achieves the desired results without adversely affecting other properties of the article.

By way of example, an article such as a surgeon's glove or condom made of latex rubber in accordance with conventional methods is subjected to a treatment wherein it is exposed to a halogen gas at a predetermined concentration, for a predetermined period of time and at a predetermined temperature and pressure. More specifically, after it is manufactured the article is placed in a chamber and fluorine gas is introduced to effect reaction between the gas and the article. In particular, a quantity of previously manufactured gloves or condoms are placed in bulk in a box or other container which is then positioned in a fluorination chamber and exposed to a low level of fluorine gas. Specifically, the articles are subjected to Fluoro-Seal, Inc's., "level 1" treatment, after which the gloves or condoms are removed from the chamber. The gloves and condoms are ready for use without the need for further treatment.

In carrying out the treatment, the gloves or condoms are placed in a vacuum chamber, e.g., Fluoro-Seal's vacuum chamber, after which the chamber is sealed and purged to remove extraneous gasses, in accordance with conventional practice. A gaseous mixture containing fluorine, e.g., fluorine and nitrogen, is then introduced into the chamber under a pressure and temperature, and at a fluorine concentration and for an interval of time commensurate with Fluoro-Seal's "level 1" treatment protocol. Following this "level 1" treatment, the chamber is purged of remaining fluorine gas and the gloves are removed.

If desired, the gloves or condoms may be agitated or tumbled in the reaction chamber to insure uniform contact between the reaction gas and the articles. For instance, a rotating drum much like a clothes dryer may be installed or placed in the reaction chamber, and the gloves or condoms placed in the drum so that they can be tumbled or agitated while being exposed to the gas.

Alternatively, directional gas jets may be used to form gas currents that develop forces which tumble or agitate the articles.

As a still further alternative, a reactive gas may be contacted with the gloves during the manufacturing process, thereby eliminating the need for a separate treatment step following manufacture.

The treatment process of the invention is simple and economical, and articles treated in accordance with the invention retain their natural color and other desirable attributes, while undergoing improvement in shelf life, barrier properties, and tear resistance.

While particular embodiments of the invention have been illustrated and described in detail herein, it should be understood that various changes and modifications may be made to the invention without departing from the spirit and intent of the invention as defined by the scope of the appended claims.

What is claimed is:

1. A process for treating natural rubber latex articles to alter the characteristics thereof and improve the resistance to passage therethrough of harmful agents, without requiring the use of separate coatings, wherein:

a plurality of said articles are placed loosely in a container, the container is placed in a chamber, the chamber is sealed and purged of extraneous agents, and a reactive gas comprising a mixture of fluorine gas and another gas or gases is introduced into the chamber under predetermined pressure and temperature, and at a predetermined concentration and for a predetermined period of time, to alter the characteristics and improve the barrier to passage therethrough of harmful agents.

2. A process as claimed in claim 1, wherein:

the articles comprise gloves.

3. A process as claimed in claim 1, wherein:

the articles comprise condoms.

4. A process as claimed in claim 3, wherein:

the condoms are rolled up.

* * * * *